United States Patent
Chaki et al.

(10) Patent No.: US 11,312,673 B2
(45) Date of Patent: Apr. 26, 2022

(54) METHOD FOR PRODUCING 1,1,2-TRIFLUOROETHANE (HFC-143)

(71) Applicant: DAIKIN INDUSTRIES, LTD., Osaka (JP)

(72) Inventors: Takehiro Chaki, Osaka (JP); Tsubasa Nakaue, Osaka (JP); Megumi Kushida, Osaka (JP); Kazuhiro Takahashi, Osaka (JP)

(73) Assignee: DAIKIN INDUSTRIES, LTD., Osaka (JP)

(*) Notice: Subject to any disclaimer, the term of this patent is extended or adjusted under 35 U.S.C. 154(b) by 0 days.

(21) Appl. No.: 17/227,601

(22) Filed: Apr. 12, 2021

(65) Prior Publication Data

US 2021/0230086 A1 Jul. 29, 2021

Related U.S. Application Data

(63) Continuation of application No. PCT/JP2020/006873, filed on Feb. 20, 2020.

(30) Foreign Application Priority Data

Feb. 22, 2019 (JP) .............. JP2019-030321

(51) Int. Cl.
| | | |
|---|---|---|
| *C07C 17/20* | (2006.01) | |
| *C07C 19/08* | (2006.01) | |
| *B01J 23/18* | (2006.01) | |
| *B01J 23/26* | (2006.01) | |

(52) U.S. Cl.
CPC .............. *C07C 17/206* (2013.01); *B01J 23/18* (2013.01); *B01J 23/26* (2013.01); *C07C 19/08* (2013.01)

(58) Field of Classification Search
CPC ...................................................... C07C 17/25
See application file for complete search history.

(56) References Cited

U.S. PATENT DOCUMENTS

| | | | | |
|---|---|---|---|---|
| 3,342,881 A | * | 9/1967 | Sasakura | ............ C07C 17/206 570/165 |
| 3,432,562 A | * | 3/1969 | Gardner | ............ C07C 21/18 570/156 |
| 4,766,258 A | * | 8/1988 | Komatsu | ............ C07C 17/206 570/165 |
| 5,059,729 A | | 10/1991 | Gervasutti | |
| 2010/0268002 A1 | | 10/2010 | Nose et al. | |
| 2017/0267612 A1 | | 9/2017 | Bonnet et al. | |

FOREIGN PATENT DOCUMENTS

| | | | |
|---|---|---|---|
| CN | 111116304 A | * | 5/2020 |
| EP | 3 792 236 | | 3/2021 |
| JP | 1-287044 | | 11/1989 |
| JP | 2014-520109 | | 8/2014 |
| JP | 2019-196312 | | 11/2019 |
| WO | 2009/078234 | | 6/2009 |
| WO | 2012/170239 | | 12/2012 |
| WO | 2015/082812 | | 6/2015 |
| WO | 2016/069785 | | 5/2016 |
| WO | 2017/104828 | | 6/2017 |

OTHER PUBLICATIONS

WO2019216239A1, translation, Published Nov. 11, 2019, pp. 1-6 (Year: 2019).*
CN111116304A, translation, Published May 8, 2020, pp. 1-9 (Year: 2020).*
International Search Report dated May 26, 2020 in International (PCT) Application No. PCT/JP2020/006873.
McBee et al., "Fluorinated Derivatives of Ethane", Industrial and Engineering Chemistry, 1947, vol. 39, No. 3, pp. 409-412.
Ishikawa et al., "Fluorine compound—Its chemisuy and application", "2.4 HF Addition to Olefins", Kodansha Ltd., 1979, pp. 80-91, with partial English translation.

* cited by examiner

*Primary Examiner* — Medhanit W Bahta
(74) *Attorney, Agent, or Firm* — Wenderoth, Lind & Ponack, L.L.P.

(57) ABSTRACT

The present disclosure provides a method for producing HFC-143 that is not expensive, and that is more efficient than conventional methods. Specifically, the present disclosure provides a method for producing 1,1,2-trifluoroethane (HFC-143) that includes contacting at least one chlorine-containing compound selected from the group consisting of 1,1,2-trichloroethane (HCC-140), 1,2-dichloro-1-fluoroethane (HCFC-141), 1,1-dichloro-2-fluoroethane (HCFC-141a), (E,Z)-1,2-dichloroethylene (HCO-1130 (E,Z)), and (E,Z)-1-chloro-2-fluoroethylene (HCFO-1131 (E,Z)) with hydrogen fluoride to perform one or more fluorination reactions, thereby obtaining a reaction gas containing HFC-143, hydrogen chloride, and hydrogen fluoride.

10 Claims, No Drawings

METHOD FOR PRODUCING 1,1,2-TRIFLUOROETHANE (HFC-143)

TECHNICAL FIELD

The present disclosure relates to a method for producing 1,1,2-trifluoroethane (HFC-143).

BACKGROUND ART

Fluoroethanes, such as 1,1,2-trifluoroethane ($CHF_2CH_2F$; "HFC-143" below), are known as a starting material for producing various refrigerants. For example, HFC-143 is known as a starting material for producing 1,2-difluoroethylene (HFO-1132).

A variety of methods for producing a fluoroethane such as HFC-143 have been proposed. For example, PTL 1 proposes a technique to produce HFC-143 by performing a hydrogenation reaction of chlorotrifluoroethylene (CTFE) in the presence of a hydrogenation catalyst. PTL 2 also discloses a technique to produce 2-chloro-1,1-difluoroethane (HCFC-142) from 1,1,2-trichloroethane (HCC-140), and discloses that a small amount of HFC-143 is mixed as a by-product.

CITATION LIST

Patent Literature
PTL 1: JPH01-287044A
PTL 2: WO2015/082812A

SUMMARY

A method for producing 1,1,2-trifluoroethane (HFC-143) comprises contacting at least one chlorine-containing compound selected from the group consisting of 1,1,2-trichloroethane (HCC-140), 1,2-dichloro-1-fluoroethane (HCFC-141), 1,1-dichloro-2-fluoroethane (HCFC-141a), (E,Z)-1,2-dichloroethylene (HCO-1130 (E,Z)), and (E,Z)-1-chloro-2-fluoroethylene (HCFO-1131 (E,Z)) with hydrogen fluoride to perform one or more fluorination reactions, thereby obtaining a reaction gas containing HFC-143, hydrogen chloride, and hydrogen fluoride.

ADVANTAGEOUS EFFECTS

The method for producing HFC-143 according to the present disclosure produces HFC-143 at low cost, and more efficiently than conventional methods.

DESCRIPTION OF EMBODIMENTS

A feature of the method for producing HFC-143 according to the present disclosure is that the method includes contacting at least one chlorine-containing compound selected from the group consisting of 1,1,2-trichloroethane (HCC-140), 1,2-dichloro-1-fluoroethane (HCFC-141), 1,1-dichloro-2-fluoroethane (HCFC-141a), (E,Z)-1,2-dichloroethylene (HCO-1130 (E,Z)), and (E,Z)-1-chloro-2-fluoroethylene (HCFO-1131 (E,Z)) with hydrogen fluoride to perform one or more fluorination reactions, thereby obtaining a reaction gas containing HFC-143, hydrogen chloride, and hydrogen fluoride.

Due to such a feature, the method for producing HFC-143 according to the present disclosure can produce HFC-143 at low cost, and more efficiently than conventional methods.

The production method according to the present disclosure uses as a starting material compound at least one chlorine-containing compound selected from the group consisting of HCC-140, HCFC-141, HCFC-141a, HCO-1130 (E,Z), and HCFO-1131 (E,Z). "(E,Z)" indicates that a compound to which "(E,Z)" is attached includes its E-form and/or Z-form. These chlorine-containing compounds, which are all available at lower prices than CTFE, can reduce the cost of producing HFC-143. Of these chlorine-containing compounds, at least either HCC-140 or HCO-1130 (E,Z) is preferable from the standpoint of starting material cost.

A feature of the production method according to the present disclosure is that the method includes contacting the above-described chlorine-containing compound with hydrogen fluoride to perform one or more fluorination reactions, thereby obtaining a reaction gas containing HFC-143, hydrogen chloride, and hydrogen fluoride.

The one or more fluorination reactions performed with hydrogen fluoride may be a gas-phase reaction or a liquid-phase reaction. The fluorination reaction that is performed until HFC-143 is obtained may be one fluorination reaction or two or more fluorination reactions, depending on the chlorine-containing compound for use.

In the case of a gas-phase reaction, it is sufficient if the chlorine-containing compound and the hydrogen fluoride both in their gas form come into contact with each other within the reaction temperature range described later. The chlorine-containing compound may be in liquid form when being supplied.

For example, a chlorine-containing compound in liquid foam at room temperature under ordinary pressure is vaporized with a vaporizer, and then allowed to pass through a preheating region; and supplied to a mixing region in which the chlorine-containing compound is brought into contact with hydrogen fluoride, thereby performing a reaction in a gas phase. Alternatively, a chlorine-containing compound in liquid form may be supplied to a reactor, and vaporized when the chlorine-containing compound has reached a region within which the compound is reactive with the hydrogen fluoride to cause a reaction.

The hydrogen fluoride for use is preferably anhydrous hydrogen fluoride, from the standpoint of suppressing the corrosion of the reactor or the degradation of the catalyst.

The method for vaporizing a chlorine-containing compound in a reaction region can be any method, and may be selected from a wide range of known methods. For example, the following method may be used. A reaction tube is filled with a material that is excellent in heat conductance, has no catalytic activity in a fluorination reaction, and is stable against hydrogen fluoride, such as nickel beads and Hastelloy pieces. The temperature distribution inside the reaction tube is then made uniform, and the reaction tube is heated to a temperature equal to or higher than the vaporization temperature of the chlorine-containing compound. The chlorine-containing compound in liquid form is supplied to the reactor tube, and vaporized so as to transform into a gas phase.

The method for supplying hydrogen fluoride to a reactor can be any method. For example, hydrogen fluoride in a gas phase can be supplied to a reactor together with a chlorine-containing compound. The amount of hydrogen fluoride to be supplied is the following: the molar ratio of the hydrogen fluoride to the chlorine-containing compound (1 mol) is preferably 20 or more, more preferably 30 or more, and still more preferably 40 or more (in particular, over 40). The upper limit of the molar ratio is, although not limited to, preferably about 60 from the standpoint of energy cost and productivity.

A molar ratio within these ranges enables both the chlorine-containing compound conversion and HFC-143 selectivity to be maintained within a more efficient (excellent) range than conventional methods. In particular, supplying 40 mol or more (in particular, over 40 mol) of hydrogen fluoride per mol of a chlorine-containing compound can significantly increase the selectivity for HFC-143.

In the present specification, "conversion" refers to the proportion (mol %) of the total mol of the compounds other than the compounds described above contained in an outflow gas (i.e., a reaction gas) coming from the outlet of the reactor relative to the mol of the chlorine-containing compound supplied to the reactor.

In the present specification, "selectivity" refers to the proportion (mol %) of the mol of the target compound (HFC-143) contained in an outflow gas (i.e., a reaction gas) coming from the outlet of the reactor relative to the total mol of the compounds other than the compounds described above.

In a fluorination reaction in a gas phase, the chlorine-containing compound as a starting material compound may be supplied to a reactor as is; or the chlorine-containing compound may be diluted with an inert gas such as nitrogen, helium, or argon, and then supplied to the reactor.

A fluorination reaction in the presence of a catalyst in a gas phase can use any known gas-phase fluorination catalyst selected from a wide range of such catalysts. Examples include oxides, hydroxides, halides, halogen oxides, and inorganic salts of chromium, aluminum, cobalt, manganese, nickel, or iron; and mixtures thereof. Of these, in order to increase the conversion of the chlorine-containing compound, chromium-based catalysts such as $CrO_2$, $Cr_2O_3$, $FeCl_3/C$, $Cr_2O_3/Al_2O_3$, $Cr_2O_3/AlF_3$, $Cr_2O_3/C$, and $CoCl_2/Cr_2O_3$ are preferable for use. The chromium oxide/aluminum oxide-based catalysts for use are preferably those disclosed in U.S. Pat. No. 5,155,082, specifically a chromium oxide/aluminum oxide catalyst (e.g., $Cr_2O_3/Al_2O_3$); and those obtained by combining a halide of cobalt, nickel, manganese, rhodium, or ruthenium with such a chromium oxide/aluminum oxide catalyst. Specifically, in the case of a gas-phase reaction, the catalyst is preferably at least partly a chromium-based catalyst.

The metallic catalyst for use may be a partly or entirely crystallized catalyst, or an amorphous catalyst. The crystallizability can be suitably selected. For example, chromium oxide with a variety of particle sizes is commercially available. To control the particle size and crystallizability, a metallic catalyst may be prepared by precipitating chromium hydroxide from chromium nitrate and ammonia, and burning the precipitate. The catalyst for use may be a single catalyst, or a mixture of two or more catalysts. The carrier for use may be, for example, a variety of activated carbon, magnesium oxide, zirconia oxide, or alumina. These catalysts may be subjected to fluorination treatment using, for example, anhydrous hydrogen fluoride or a fluorine-containing compound before they are used in a fluorination reaction. In particular, these catalysts are preferably subjected to fluorination treatment using anhydrous hydrogen fluoride.

The form of the reactor for use can be any form; the reactor for use can be selected from a wide range of known reactors. For example, a tube-form flow reactor filled with a catalyst can be used. In a reaction in the absence of a catalyst, the reactor for use can be, for example, an adiabatic reactor with a void-tower, or an adiabatic reactor filled with a porous or non-porous metal or medium for increasing the degree of mixture of the hydrogen fluoride and the starting material in their gas phase. Alternatively, the reactor for use is preferably, for example, a multi-tube reactor from which heat is removed by using a heat medium and/or whose temperature distribution is made uniform.

In the use of a reactor with a void-tower, for example, the relationship between the flow rate of a chlorine-containing compound and the inner diameter of a reaction tube is preferably set such that the linear velocity is high and the heat-transfer area is large, in order to improve heat-transfer efficiency using a reaction tube with a small inner diameter.

The reaction temperature in a gas-phase fluorination reaction as a temperature inside the reactor is preferably 150 to 600° C., more preferably 200 to 500° C., and still more preferably 230 to 400° C. Setting the reaction temperature to 200° C. or more can improve the selectivity for a target product. A reaction temperature of 600° C. or less can reduce the risk such that carbides are formed by the reaction, and that these carbides adhere to and/or accumulate on the reaction tube wall or on the filler to gradually block the reactor. However, if such a risk is involved, carbides remaining in the reaction tube can be removed through combustion by entraining oxygen into the reaction system, or by temporarily stopping the reaction to allow oxygen or air to circulate.

The reaction pressure in a gas-phase fluorination reaction can be any pressure under which a chlorine-containing compound and hydrogen fluoride can exist in their gas phase. The reaction pressure can be an ordinary pressure, increased pressure, or decreased pressure. For example, the reaction can be performed under reduced pressure or atmospheric pressure (0 MPaG); the reaction can also be performed under increased pressure, as long as the starting materials do not transform into liquid. Typically, the reaction pressure is preferably within the range of 0 to 2 MPaG, and more preferably 0 to 1 MPaG.

The reaction time for the gas-phase fluorination reaction can be any time. Typically, the contact time represented by W/Fo (the ratio of the catalyst added W (g) to the total flow rate Fo (flow rate at 0° C. under 0.0 MPaG: cc/sec) of the starting material gas that is allowed to flow in a reaction system) is about 0.1 to 100 g·sec/cc, and preferably about 5 to 50 g·sec/cc. The total flow rate of the starting material gas in this case refers to the sum of the total flow rate of the chlorine-containing compound and the hydrogen fluoride (starting materials), and the flow rate of inert gas, oxygen, or the like, when such an optional component is added.

The liquid-phase catalyst for use in performing a fluorination reaction in the presence of a catalyst in a liquid phase can be any catalyst, and can be selected from a wide range of known liquid-phase fluorination catalysts. Specifically, the liquid-phase catalyst for use may be at least one member selected from the group consisting of Lewis acid, transition metal halides, transition metal oxides, halides of the metals of the group IVb, and halides of the metals of the group Vb.

More specifically, the liquid-phase catalyst for use may be at least one member selected from the group consisting of antimony halides, tin halides, tantalum halides, titanium halides, niobium halides, molybdenum halides, iron halides, halogenated chromium fluoride, and oxidized chromium fluoride.

More specifically, the liquid-phase catalyst for use is preferably $SbCl_5$, $SbCl_3$, $SbF_5$, $SnCl_4$, $TaCl_5$, $TiCl_4$, $NbCl_5$, $MoCl_6$, and $FeCl_3$; and those prepared from a chloride salt and hydrogen fluoride, such as $SbCl_{(5-y)}F_y$, $SbCl_{(3-y)}F_y$, $SnCl_{(4-y)}F_y$, $TaCl_{(5-y)}F_y$, $TiCl_{(4-y)}F_y$, $NbCl_{(5-y)}F_y$, $MoCl_{(6-y)}F_y$, and $FeCl_{(3-y)}F_y$ (the lower limit of y is 0.1 or more, and the upper limit of y is equal to or lower than the valence of individual elements). These catalysts can be used singly, or in a combination of two or more. Of these, catalysts that are at least partly an antimony-based catalyst are preferable, and antimony pentachloride is particularly preferable.

These catalysts can be easily renewed by a known technique when they have become inactive. A usable method for renewing such a catalyst is bringing chlorine into contact with the catalyst. For example, chlorine in an amount of about 0.15 to 25 g/hr may be added per 100 g of a liquid-phase fluorination catalyst in a liquid-phase reaction.

The reaction temperature in a liquid-phase fluorination reaction as a temperature inside a reaction system is preferably 50 to 200° C., and more preferably 80 to 150° C. Setting the reaction temperature to 80° C. or more can increase the selectivity for a target product and productivity. The pressure in a liquid-phase fluorination reaction is preferably within the range of 0 to 2 MPaG, and more preferably 0 to 1 MPaG as in a gas-phase reaction.

The reactor for use in both the gas-phase fluorination reaction and the liquid-phase fluorination reaction can be any reactor, and can be selected from a wide range of known reactors. Specifically, the reactor for use is preferably one formed of a material that is resistant to corrosive action by hydrogen fluoride, such as Hastelloy, Inconel, Monel, or Incoloy.

After a reaction gas containing HFC-143, hydrogen chloride, and hydrogen fluoride is obtained by the production method according to the present disclosure, HFC-143 can be obtained by using various known separation methods. The hydrogen fluoride can be recycled in a fluorination reaction. The obtained HFC-143 can be optionally subjected to purification treatment, and then used for various purposes. For example, 1,2-difluoroethylene (HFO-1132) may be produced by subjecting HFC-143 to a dehydrofluorination reaction. From this perspective, the present disclosure also includes a disclosure related to a method for producing 1,2-difluoroethylene (HFO-1132) that includes subjecting 1,1,2-trifluoroethane (HFC-143) contained in the reaction gas obtained by the above-described production method according to the present disclosure to a dehydrofluorination reaction. This method for producing HFO-1132 can also be described as "a method for producing 1,2-difluoroethylene (HFO-1132) comprising performing the production method according to the present disclosure, and subjecting 1,1,2-trifluoroethane (HFC-143) contained in the obtained reaction gas to a dehydrofluorination reaction."

Embodiments of the present disclosure have been described above. However, the present disclosure is not limited to these embodiments in any way. Various modifications may be made without departing from the spirit and principal concept of the present disclosure.

As described above, the present disclosure includes the following.

1. A method for producing 1,1,2-trifluoroethane (HFC-143), the method comprising
    contacting at least one chlorine-containing compound selected from the group consisting of 1,1,2-trichloroethane (HCC-140), 1,2-dichloro-1-fluoroethane (HCFC-141), 1,1-dichloro-2-fluoroethane (HCFC-141a), (E,Z)-1,2-dichloroethylene (HCO-1130 (E,Z)), and (E,Z)-1-chloro-2-fluoroethylene (HCFO-1131 (E,Z)) with hydrogen fluoride to perform one or more fluorination reactions, thereby obtaining a reaction gas containing HFC-143, hydrogen chloride, and hydrogen fluoride.

2. The production method according to Item 1, wherein the one or more fluorination reactions are performed under a pressure of 0 to 2 MPaG.
3. The production method according to Item 1 or 2, wherein the one or more fluorination reactions are performed in the presence of a catalyst in a gas phase.
4. The production method according to Item 3, wherein the one or more fluorination reactions are performed at a temperature of 150 to 600° C.
5. The production method according to Item 3 or 4, wherein the contact time W/Fo between the at least one chlorine-containing compound and the hydrogen fluoride is 0.1 to 100 g·sec/cc in the one or more fluorination reactions.
6. The production method according to any one of Items 1 to 5, wherein the molar ratio of the hydrogen fluoride to the at least one chlorine-containing compound in the one or more fluorination reactions is 20 or more.
7. The production method according to any one of Items 1 to 5, wherein the molar ratio of the hydrogen fluoride to the at least one chlorine-containing compound in the one or more fluorination reactions is over 40.
8. The production method according to any one of Items 3 to 7, wherein the catalyst is at least partly a chromium-based catalyst.
9. The production method according to Item 1 or 2, wherein the one or more fluorination reactions are performed in the presence of a catalyst in a liquid phase.
10. The production method according to Item 9, wherein the catalyst is at least partly an antimony-based catalyst.
11. A method for producing 1,2-difluoroethylene (HFO-1132), the method comprising subjecting 1,1,2-trifluoroethane (HFC-143) contained in the reaction gas obtained by the production method of any one of claims 1 to 10 to a dehydrofluorination reaction.

EXAMPLES

Embodiments of the present disclosure are described in more detail below with reference to Examples. However, the present disclosure is not limited to the scope of the Examples.

Example 1

A chromium fluoride oxide catalyst was prepared in accordance with the following procedure. First, chromium oxide represented by CrxOy was prepared in accordance with the method disclosed in JPH05-146680A. Specifically, 10% ammonia water was added to 765 g of a 5.7% aqueous chromium nitrate solution; and the thus-formed precipitate was collected by filtration, followed by washing and then drying in air at 120° C. for 12 hours, thereby obtaining chromium hydroxide. This chromium hydroxide was then famed into pellets with a diameter of 3.0 mm and a height of 3.0 mm. The pellets were then burned in a nitrogen stream at 400° C. for 2 hours, thereby obtaining chromium oxide. The obtained chromium oxide had a specific surface area (according to the BET theory) of about 200 m$^2$/g. Subsequently, this chromium oxide was subjected to fluorination treatment to obtain a chromium fluoride oxide catalyst. Specifically, while a hydrogen fluoride-containing gas was allowed to flow into chromium oxide, the temperature was increased to 200 to 360° C. incrementally to heat the chromium oxide. After the temperature reached 360° C., fluorination was performed using hydrogen fluoride for 2 hours, thereby obtaining a chromium fluoride oxide catalyst.

A tubular Hastelloy reactor with an inner diameter of 15 mm and a length of 1 m was then charged with 12 g of the obtained chromium fluoride oxide catalyst.

This reaction tube was maintained at 150° C. under atmospheric pressure (0.0 MPaG). Anhydrous hydrogen fluoride (HF) gas was supplied to the reactor at a flow rate of 118 mL/min (flow rate at 0° C. under 0.0 MPaG), and the reactor was maintained for 1 hour. Thereafter, $CHCl_2CH_2Cl$ (HCC-140) was supplied at a flow rate of 2.4 mL/min (gas flow rate at 0° C. under 0.0 MPaG). In this case, the molar ratio, HF:HCC-140, was 50:1, and the contact time W/Fo was 6 g·sec/cc.

After 1.5 hours from the start of the reaction, the conversion of HCC-140 was 56.4%, and the selectivity for HFC-143 was 0.4%.

Example 2

HFC-143 was synthesized in the same manner as in Example 1, except that the reaction temperature was changed to 240° C.

After 2.5 hours from the start of the reaction, the conversion of HCC-140 was 99.8%, and the selectivity for HFC-143 was 2.4%.

Example 3

HFC-143 was synthesized in the same manner as in Example 1, except that the reaction temperature was changed to 280° C.

After 2.5 hours from the start of the reaction, the conversion of HCC-140 was 100%, and the selectivity for HFC-143 was 6.5%.

Example 4

HFC-143 was synthesized in the same manner as in Example 1, except that the reaction temperature was changed to 330° C.

After 1.5 hours from the start of the reaction, the conversion of HCC-140 was 100%, and the selectivity for HFC-143 was 4.1%.

Example 5

HFC-143 was synthesized in the same manner as in Example 1, except that anhydrous hydrogen fluoride (HF) gas was supplied to the reactor at a flow rate of 57.4 mL/min (flow rate at 0° C. under 0.0 MPaG), and the reaction temperature was changed to 200° C. In this case, the molar ratio, HF:HCC-140, was 24.3:1, and the contact time W/Fo was 12 g·sec/cc.

After 2 hours from the start of the reaction, the conversion of HCC-140 was 98.3%, and the selectivity for HFC-143 was 0.1%.

Example 6

HFC-143 was synthesized in the same manner as in Example 5, except that the reaction temperature was changed to 240° C.

After 3 hours from the start of the reaction, the conversion of HCC-140 was 100%, and the selectivity for HFC-143 was 1.9%.

Example 7

HFC-143 was synthesized in the same manner as in Example 5, except that the reaction temperature was changed to 280° C.

After 2 hours from the start of the reaction, the conversion of HCC-140 was 100%, and the selectivity for HFC-143 was 2.7%.

Example 8

HFC-143 was synthesized in the same manner as in Example 1, except that anhydrous hydrogen fluoride (HF) gas was supplied to the reactor at a flow rate of 35 mL/min (flow rate at 0° C. under 0.0 MPaG), and the reaction temperature was changed to 280° C. In this case, the molar ratio, HF:HCC-140, was 15:1, and the contact time W/Fo was 19 g·sec/cc.

After 2 hours from the start of the reaction, the conversion of HCC-140 was 100%, and the selectivity for HFC-143 was 1.4%.

The results of Example 8 indicate that because a low molar ratio led to a reduced yield of HFC-143, the yield of HFC-143 can be increased by setting the molar ratio to 20 or more, preferably 40 or more (in particular, over 40).

Example 9

HFC-143 was synthesized in the same manner as in Example 8, except that the reaction temperature was changed to 365° C.

After 2 hours from the start of the reaction, the conversion of HCC-140 was 100%, and the selectivity for HFC-143 was 0.27%.

Example 10

A tubular Hastelloy reactor with an inner diameter of 15 mm and a length of 1 m was charged with 12 g of the chromium fluoride oxide catalyst prepared in Example 1.

This reaction tube was maintained at 240° C. under atmospheric pressure (0.0 MPaG). Anhydrous hydrogen fluoride (HF) gas was supplied to the reactor at a flow rate of 63 mL/min (flow rate at 0° C. under 0.0 MPaG), and the reactor was maintained for 1 hour. Thereafter, CHClCHCl (HCO-1130) was supplied at a flow rate of 3 mL/min (gas flow rate at 0° C. under 0.0 MPaG). In this case, the molar ratio, HF:HCO-1130, was 21:1, and the contact time W/Fo was 11 g·sec/cc.

After 19 hours from the start of the reaction, the conversion of HCO-1130 was 29%, and the selectivity for HFC-143 was 6.8%.

Example 11

HFC-143 was synthesized in the same manner as in Example 10, except that anhydrous hydrogen fluoride (HF) gas was supplied to the reactor at a flow rate of 61.9 mL/min (flow rate at 0° C. under 0.0 MPaG), and HCO-1130 was supplied to the reactor at a flow rate of 4.1 mL/min (gas flow rate at 0° C. under 0.0 MPaG). In this case, the molar ratio, HF:HCO-1130, was 15:1, and the contact time W/Fo was 11 g·sec/cc.

After 2 hours from the start of the reaction, the conversion of HCO-1130 was 25.5%, and the selectivity for HFC-143 was 3.3%.

Example 12

HFC-143 was synthesized in the same manner as in Example 10, except that anhydrous hydrogen fluoride (HF) gas was supplied to the reactor at a flow rate of 64.7 mL/min (flow rate at 0° C. under 0.0 MPaG), and HCO-1130 was supplied to the reactor at a flow rate of 1.3 mL/min (gas flow rate at 0° C. under 0.0 MPaG). In this case, the molar ratio, HF:HCO-1130, was 50:1, and the contact time W/Fo was 11 g·sec/cc.

After 2 hours from the start of the reaction, the conversion of HCO-1130 was 63.5%, and the selectivity for HFC-143 was 14.6%.

A comparison between the results of Example 11 and the results of Example 10 and Example 12 indicates that because a low molar ratio led to a reduced yield of HFC-143, the yield of HFC-143 can be increased by setting the molar ratio to 20 or more, preferably 40 or more (in particular, over 40).

Example 13

HFC-143 was synthesized in the same manner as in Example 10, except that anhydrous hydrogen fluoride (HF) gas was supplied to the reactor at a flow rate of 150 mL/min (flow rate at 0° C. under 0.0 MPaG), HCO-1130 was supplied to the reactor at a flow rate of 3 mL/min (gas flow rate at 0° C. under 0.0 MPaG), the reaction pressure was changed to 0.6 MPaG, and the reaction temperature was changed to 200° C. In this case, the molar ratio, HF:HCO-1130, was 50:1, and the contact time W/Fo was 4.7 g·sec/cc.

After 2 hours from the start of the reaction, the conversion of HCO-1130 was 40%, and the selectivity for HFC-143 was 5.9%.

Example 14

HFC-143 was synthesized in the same manner as in Example 13, except that the reaction pressure was changed to 0.0 MPaG.

After 2 hours from the start of the reaction, the conversion of HCO-1130 was 25.4%, and the selectivity for HFC-143 was 7.4%.

A comparison between the results of Example 13 and the results of Example 14 indicates that the conversion can be greatly increased by increasing the pressure to 0.6 MPaG.

Example 15

Under the conditions in Example 14, 1% of $O_2$ relative to the total flow rate was entrained.

After 15 hours from the start of the reaction, the conversion of HCO-1130 was 44.2%, and the selectivity for HFC-143 was 17.8%.

Example 16

HFC-143 was synthesized in the same manner as in Example 15, except that the reaction temperature was changed to 260° C.

After 2 hours from the start of the reaction, the conversion of HCO-1130 was 54%, and the selectivity for HFC-143 was 17.5%.

Example 17

HFC-143 was synthesized in the same manner as in Example 15, except that the reaction temperature was changed to 280° C.

After 2 hours from the start of the reaction, the conversion of HCO-1130 was 55.4%, and the selectivity for HFC-143 was 18.2%.

A comparison between the results of Example 14 and the results of Examples 15 to 17 indicates that adding oxygen can increase not only the conversion, but also the selectivity for HFC-143.

The invention claimed is:

1. A method for producing 1,1,2-trifluoroethane (HFC-143), the method comprising
contacting in a gas phase at least one chlorine-containing compound selected from the group consisting of 1,1,2-trichloroethane (HCC-140), 1,2-dichloro-1-fluoroethane (HCFC-141), 1,1-dichloro-2-fluoroethane (HCFC-141a), (E,Z)-1,2-dichloroethylene (HCO-1130 (E,Z)), and (E,Z)-1-chloro-2-fluoroethylene (HCFO-1131 (E,Z)) with hydrogen fluoride to perform one or more fluorination reactions, thereby obtaining a reaction gas containing HFC-143, hydrogen chloride, and hydrogen fluoride,
wherein the contact time W/Fo between the at least one chlorine-containing compound and the hydrogen fluoride is 0.1 to 100 g·sec/cc in the one or more fluorination reactions.

2. The production method according to claim 1, wherein the one or more fluorination reactions are performed under a pressure of 0 to 2 MPaG.

3. The production method according to claim 1, wherein the one or more fluorination reactions are performed in the presence of a catalyst.

4. The production method according to claim 3, wherein the catalyst is at least partly a chromium-based catalyst.

5. The production method according to claim 1, wherein the one or more fluorination reactions are performed at a temperature of 150 to 600° C.

6. The production method according to claim 1, wherein the molar ratio of the hydrogen fluoride to the at least one chlorine-containing compound in the one or more fluorination reactions is 20 or more.

7. The production method according to claim 1, wherein the molar ratio of the hydrogen fluoride to the at least one chlorine-containing compound in the one or more fluorination reactions is over 40.

8. A method for producing 1,2-difluoroethylene (HFO-1132), the method comprising producing 1,1,2-trifluoroethane (HFC-143) by the production method of claim 1, and subjecting the 1,1,2-trifluoroethane (HFC-143) contained in the reaction gas obtained by the production method of claim 1 to a dehydrofluorination reaction.

9. A method for producing 1,1,2-trifluoroethane (HFC-143), the method comprising
contacting in a liquid phase at least one chlorine-containing compound selected from the group consisting of 1,2-dichloro-1-fluoroethane (HCFC-141), 1,1-dichloro-2-fluoroethane (HCFC-141a), (E,Z)-1,2-dichloroethylene (HCO-1130 (E,Z)), and (E,Z)-1-chloro-2-fluoroethylene (HCFO-1131 (E,Z)) with hydrogen fluoride to perform one or more fluorination reactions, thereby obtaining a reaction gas containing HFC-143, hydrogen chloride, and hydrogen fluoride,
wherein the one or more fluorination reactions are performed in the presence of a catalyst, and the catalyst is at least partly an antimony-based catalyst.

10. A method for producing 1,2-difluoroethylene (HFO-1132), the method comprising producing 1,1,2-trifluoroethane (HFC-143) by the production method of claim 9, and subjecting the 1,1,2-trifluoroethane (HFC-143) contained in the reaction gas obtained by the production method of claim 9 to a dehydrofluorination reaction.

\* \* \* \* \*